United States Patent [19]

Saari

[11] 3,976,782
[45] Aug. 24, 1976

[54] 3-(2,5-DIHYDROXYPHENYL)-ALANINE AS A CARDIAC STIMULANT

[75] Inventor: Walfred S. Saari, Lansdale, Pa.

[73] Assignee: Merck & Co., Inc., Rahway, N.J.

[22] Filed: Mar. 25, 1975

[21] Appl. No.: 561,822

[52] U.S. Cl. .................................................. 424/319
[51] Int. Cl.² ....................................... A61K 31/195
[58] Field of Search ................................... 424/319

[56] References Cited
OTHER PUBLICATIONS

Journal of the American Chemical Society, 71, p. 3758 (1949).
Journal of the American Chemical Society, 76, p. 133 (1954).
Biochemical Journal, 43, p. 599 (1948).
Circulation, XLV, pp. 97–106, (1972).

Primary Examiner—Leonard Schenkman
Assistant Examiner—Daren M. Stephens
Attorney, Agent, or Firm—David L. Rose; J. Jerome Behan

[57] ABSTRACT

3-(2,5-Dihydroxyphenyl)-alanine, in its racemic form as well as the individual optical isomers thereof possess significant activity as cardiac stimulants. Various derivatives of the racemic mixture are prepared which are resolved into the component optical isomers. The racemic mixture and the enantiomers are employed in compositions which are administered as cardiac stimulants.

4 Claims, No Drawings

3-(2,5-DIHYDROXYPHENYL)-ALANINE AS A CARDIAC STIMULANT

DESCRIPTION OF THE PRIOR ART 3-(2,5-Dihydroxyphenyl)-alanine has been disclosed along with the preparation thereof in *Journal of the American Chemical Society*, 71, 3758 (1949) and *Journal of the American Chemical Society*, 76, 133 (1954). The resolution of (+) 3-(2,5-dihydroxyphenyl)-alanine into its (+) and (−) enantiomers is described in *Biochemical Journal*, 43, 599 (1948). The isomeric 3-(3,4-dihydroxyphenyl) alanine has been disclosed as having activity on the blood pressure and heart rate on intravenous injection in *Circulation* XLV, 97 et seq (1972). However, in comparison with 3-(2,5-dihydroxyphenyl)-alanine it has been discovered that the positive intropic effect of the 3,4-isomer is considerably less pronounced than that of the 2,5-isomer. There has been found no reference in the literature that 3-(2,5-dihydroxyphenyl)-alanine or its enantiomers has any cardiac stimulating properties.

SUMMARY OF THE INVENTION 3-(2,5-Dihydroxyphenyl)-alanine has been discovered to have a surprising and high degree of cardiac stimulant activity. This surprising activity has been found to be best utilized when the active compound is employed in compositions which are administered orally. Thus, it is an object of this instant invention to provide a method for utilizing 3-(2,5-dihydroxyphenyl)-alanine as a cardiac stimulant. It is also an object to utilize this compound in ether its racemic or optically active forms as such a cardiac stimulant. A still further object is to provide for compositions which utilize the active compound as a racemic mixture or as the separated enantiomers as the active ingredient. Further objects will become apparent upon reading the complete Disclosure of the Invention.

DISCLOSURE OF THE INVENTION 3-(2,5-Dihydroxyphenyl)-alanine is a known compound which has the following structural formula:

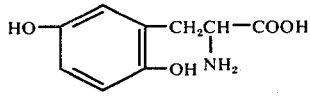

The preparation of 3-(2,5-dihydroxyphenyl)-alanine is fully described by Lambooy in the *Journal of the American Chemical Society*, 71, 3758 (1949) starting with 2,5-dihydroxybenzaldehyde and proceeding through the intermediates 3-acetamido-6-acetoxy coumarin or 2-phenyl-4-(2,5-diacetoxybenzal)-5-oxazolone.

Also included within the ambit of the instant invention are the pharmaceutically acceptable salts of 3-(2,5-dihydroxyphenyl)-alanine. The salts may be either basic salts with the carboxylic acid function of the molecule or may be acid salts with the amine function of the molecule. The preferred base salts are the alkali metal or alkaline earth metal salts such as sodium, potassium, calcium and the like. The preferred acid salts are the pharmaceutically acceptable mineral acids such as the hydrohalide, nitrate, sulfate and the like.

Also included within the ambit of the instant invention are the individual enantiomers of the racemic (+)3-(2,5-dihydroxyphenyl)-alanine. The optical isomers result from the assymetric carbon atom bearing the amine and carboxy functions. The individual enantiomers may be utilized in compositions for the treatment of heart failure since both the (+) and (−) isomers possess substantial, although not identical, cardiac stimulant activity.

The racemic mixture may be resolved into its optical isomers by reaction with an optically active molecule, fractional crystallization of the product to separate the individual diastereomers and regeneration of the optically active reactant. It has been found preferable to initially protect the amine function of 3-(2,5-dihydroxy-phenyl) alanine with an appropriate amide group. Any amide group will suitably protect the amine function and the formamide, acetamide, benzamide and others may be employed. The benzamido group, however, is preferred. In addition, it is desirable to protect the phenolic hydroxyl groups during the resolution procedure. The preferred procedure uses the methyl ether as the phenolic protective group. The preparation of DL-2-benzamido-3-(2',5'-dimethoxyphenyl) propionic acid is described by Neuberger in *Biochemical Journal*, 43, 599 (1948). One skilled in the art using analogous procedures will be able to utilize other protecting groups to suitably protect the substrate molecule.

With the molecule suitable protected the resolution is affected by reacting an optically active amine with the carboxy group of the protected amino acid. Any optically active amine will suffice for this procedure, however, (−)-α-methylbenzylamine is preferred.

The protected amino acid is dissolved in an appropriate solvent such as a loweralkanol and a molecular equivalent of the amine is added thereto. After about 5 to 30 minutes, the reaction mixture is evaporated to dryness. The residue is recrystallized many times until essentially constant optical rotation is achieved. The mother liquors from the multiple recrystallizations are combined and afford the other optical isomer using suitable multiple recrystallization techniques known to those skilled in this art.

The optically pure protected amino acid is regenerated from the recrystallized diastereomeric salts by treatment with excess equeous base, such as dilute sodium hydroxide solution, extraction to remove the resolving amine, and acidification with an aqueous mineral acid solution. The protective groups are removed by hydrolysis. Either acid or base hydrolysis may be employed to remove the amide group, however, acid hydrolysis must be employed to remove the alkyl ether protective group. Thus, acid hydrolysis is preferred since it removes both types of protective groups in a single step. Strong mineral acid solutions in glacial acetic acid heated at reflux for from 2 to 24 hours are preferred for the removal of the protective groups. Hydrohalic acids such as hydrochloric, hydrobromic, and hydroiodic acids are preferred.

When basic or mild acid conditions are employed, the process will effect the removal of the amide function only. Aqueous bases such as alkali metal hydroxide solutions heated at reflux for from 2 to 24 hours are sufficient to remove the amide protective group. However, following this procedure, the alkyl ether groups must be removed using acid catalyzed hydrolysis as described above. The optically pure isomers are isolated from the hydrolysis reaction mixture by techniques known to those skilled in this art.

3-(2,5-Dihydroxyphenyl)-alanine and the optical isomers thereof exhibit valuable pharmacological properties of an unexpectedly high degree. They primarily effect the contractile force of the heart muscle. By increasing the contractile force of the heart muscle with a resultant increase in cardiac output, these compounds afford a valuable means of treating heart failure.

Congestive heart failure results when the heart pumps less blood than is required by the metabolic demands of the body. The objectives of therapy are to restore the balance of supply and demand for blood. This can be achieved through the use of the instant cardiotonic agents which improve myocardial contractility and influence cardiac output to meet the demands of the body.

The use of current agents to stimulate the failing heart is limited by their toxic effects on the heart or by deleterious side effects on the peripheral circulation. For example although the cardiac glycosides are myocardial stimulants and can restore the failing heart, they do so at doses very close to those which produce toxic symptoms of cardiac arrhythmia, nausea and vomiting. The use of sympathomimetic agents are limited by associated arrhythmia, tachycardia, tachyphylaxis or altered peripheral resistance.

3-(2,5-Dihydroxyphenyl)-alanine and its pharmaceutically acceptable salts of this invention have been found to be significant myocardial stimulants which substantially avoid the toxic manifestations of prior art cardiac stimulants. This cardiac stimulation is observed in animals by measuring the in vitro contractile effect on isolated heart muscle and in vivo in anesthetized dogs carrying a cardiac strain gauge.

The compounds of this invention are administered to animals, including humans, with heart failure at a dose of from about 0.1 to 50 mg./kg. of body weight per day.

When (±) 3-(2,5-dihydoxyphenyl)-alanine is administered to the anesthetized dog, a significant increase in myocardial contractile force is noted. In this preparation, myocardial contractility is measured by means of a strain gauge sutured on the left ventricle. At doses from 25 ug./kg. to 2 mg./kg., i.v., an increase in the myocardial contractile force was observed with only minimal effects on mean arterial pressure or heart rate. At 5 mg./kg. i.v., there was a 133% maximal increase in contractile force at 20 minutes after treatment with a duration of action in excess of 120 minutes. In this experiment, the increase in blood pressure did not exceed 20 mm. Hg. The heart rate increased transiently by only 12 beats per minute.

The optical isomers also have a significant effect on the myocardial contractile force. Both (+) and (−) isomers are effective myocardial stimulants. At 2.5 mg./kg., i.v., the isomers possess about the same activity. At about 5 mg./kg., the (−) isomer is statistically significantly more active that the (+) isomer. These results demonstrate that the (+) and (−) isomers are independently useful compounds.

For such usage the compounds of this invention may be administered orally or parenterally as such or admixed with conventional pharmaceutical carriers. They may be administered orally in such forms as tablets, dispersible powders, granules, capsules, syrups and exlixers, and parenterally as solutions, suspensions, dispersions, emulsions, and the like, e.g., a sterile injectable aqueous suspension. The compositions for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and absorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g., calcium carbonate, calcium phosphate and kaolin. The injectable compositions are formulated as known in the art and may contain appropriate dispersing or wetting agents and suspending agents identical or similar to those mentioned above. These pharmaceutical preparations may contain up to about 90% of the active ingredient in combination with the carrier or adjuvant.

The cardiotonic effective dosage of active ingredient employed for the treatment of congestive heart failure may vary depending on the particular optical isomer employed and the severity of the condition being treated. However, in general, satisfactory results are obtained when 3-(2,5-dihydroxyphenyl)-alanine or its optical isomers are administered at a daily dosage of from about 0.1 mg. to about 50 mg./kg. of animal body weight, preferably given in divided doses two to four times a day, or in sustained release form. For most large mammals in need of said treatment, the total daily dosage is from about 0.7 to about 50 mg./kg. preferably administered orally. Dosage forms suitable for internal use comprise from about 0.1 to about 25 mg./kg. of the active compound in intimate admixture with a solid or liquid pharmaceutically acceptable carrier or diluent.

The preferred pharmaceutical compositions from the standpoint of preparation and ease of administration are solid compositions, particularly dryfilled capsules and tablets containing about 50 mg. to 2 g. of active ingredient.

EXAMPLE 1

Resolution of racemic-2-benzamido-3-(2,5-dimethoxyphenyl)-propionic acid

A solution of 59.7 g. (0.18 mole) of (±)-2-benzamido-3-(2,5-dimethoxyphenyl-propionic acid and 21.8 g. (0.18 mole) of (−)-α-methylbenzylamine in 360 ml. of warm methanol is stirred at room temperature for 5 minutes and concentrated to dryness under reduced pressure. The residue is recrystallized five times from hot water to give the (−)-α-methylbenzylamine salt of (−)-2-benzamido-3-(2,5-dimethoxyphenyl)-propionic acid with essentially constant rotation, $[\alpha]_D^{24}=(-)18.31°(C=0.95, CH_3OH)$. The resolved salt is dissolved in 600 ml. hot water, made basic with excess 5N sodium hydroxide solution and extracted with three 50 ml. portions of chloroform. The aqueous extract is acidified with 6N hydrochloric acid. The precipitate is removed by filtration and dried to give 20 g. of (−)-2-benzamido-3-(2,5-dimethoxyphenyl)-propionic acid, m.p. 170°–172°C. $[\alpha]_D^{23}=(-)34.54°(C=0.9, C_2H_5OH)$.

The mother liquors from the recrystallization of the (−)-α-methylbenzylamine salt are combined and concentrated under reduced pressure. The residue is dissolved in hot water and converted to the free acid by basification with 5N sodium hydroxide solution, chloroform extraction and acidification with 6N hydrochloric acid. A solution of this acid, 34.2 g., and 12.6 g. of (+)-α-methylbenzylamine in 200 ml. of warm methanol is concentrated to dryness under reduced pressure. After recrystallizing the residue three times from hot water, the rotation of the salt becomes essentially constant, $[\alpha]_D^{24}=(+)18.14°(C=1.0, CH_3OH)$. Neutralization of this salt as before with 5N sodium hydroxide solution, chloroform extraction and acidification with 6N hydrochloric acid gives 16.5 g. of (+)-2-benzamido-3-(2,5-dimethoxyphenyl)-propionic acid, $[\alpha]_D^{23}=(+)34.14°(C=1.75, C_2H_5OH)$.

EXAMPLE 2

(−)-3-(2,5-Dihydroxyphenyl)-alanine hydrate

A solution of 10 g. (−)-2-benzamido-3-(2,5-dimethoxyphenyl)-propionic acid in 40 ml. hydriodic acid (d.1.7) and 40 ml. glacial acetic acid is heated at reflux under an atmosphere of carbon dioxide for 3 hours. The reaction mixture is concentrated to dryness under reduced pressure, water is added and the mixture is reconcentrated. After one more addition of water and concentration, 100 ml. of water is added and filtered at 50°C. The aqueous filtrate is extracted with three portions of chloroform and one portion of ethyl ether and then concentrated under reduced pressure to approximately 50 ml. The solution is neutralized with concentrated ammonium hydroxide solution and concentrated to dryness under reduced pressure. Recrystallization from water gives (−)-3-(2,5-dihydroxyphenyl)-alanine hydrate, m.p. 223°–228°C. dec. $[\alpha]_D^{25}=(-)9.5°(C=0.375, 1N HCl)$.

EXAMPLE 3

(+)-3-(2,5-Dihydroxyphenyl)-alanine hydrate

A solution of 12 g. (+)-2-benzamido-3-(2,5-dimethoxyphenyl)-propionic acid in 120 ml. of 48% hydrobromic acid and 120 ml. of glacial acetic acid is heated at reflux under nitrogen for 5 hours. The reaction solution is concentrated to dryness under reduced pressure, 100 ml. of water is added and the solution is reconcentrated. The residue is dissolved in water and extracted with two portions of ethyl ether. After concentrating the aqueous extract under reduced pressure, water is added to bring the volume to approximately 100 ml. The pH of the solution is adjusted to 5.0 to 5.5 by the addition of concentrated ammonium hydroxide solution. Cooling and filtering gives (+)-3-(2,5-dihydroxyphenyl)-alanine hydrate, m.p. 237°–45°C. dec., $[\alpha]_D^{23}=(+)8.57°(C=1.3, 1N HCl)$.

EXAMPLE 4

Tablets suitable for oral administration which contain the following ingredients may be prepared by conventional tabletting techniques. Such tablets are useful in treating heart failure at a dose of one or two tablets 2 to 4 times a day.

| Ingredient | Weight (mg.) |
| --- | --- |
| (+) 3-(2,5-dihydroxyphenyl)-alanine | 50 |
| Tragacanth | 10 |
| Lactose | 237.5 |
| Corn Starch | 25 |
| Talcum | 15 |
| Magnesium Stearate | 2.5 |

EXAMPLE 5

Dry Filled Capsules

Capsules suitable for oral administration which contain the following ingredients are prepared in a conventional manner. Such capsules are useful as cardiac stimulants at a dose of one or two capsules 2 to 4 times a day.

| Ingredient | Weight (mg.) |
| --- | --- |
| (−)-3-(2,5-dihydroxyphenyl)-alanine | 75 |
| Inert solid diluent (starch, lactose kaolin, etc.) | 225 |

EXAMPLE 6

Sterile Suspension for Injection and Oral Liquid Suspension

The following pharmaceutical compositions are formulated with the indicated amount of active ingredient using conventional techniques. The injectable suspension and the oral liquid suspension represent formulations useful as unit doses and may be administered in the treatment of heart failure. The injectable suspension is suitable for administration once a day whereas the oral liquid suspension is suitably administered 2 to 4 times per day for this purpose.

| Ingredient | Weight (mg.) Suspension | Suspension |
| --- | --- | --- |
| (−)-3-(2,5-dihydroxyphenyl)-alanine | 50 | 100 |
| Sodium carboxymethyl-cellulose U.S.P. | 1.25 | |
| Methyl cellulose | 0.4 | |
| Polyvinyl pyrrolidone | 5 | |
| Lecithin | 3 | |
| Benzyl alcohol | 0.01 | |
| Magnesium aluminium silicate | | 47.5 |
| Flavor | | Q.S. |
| Color | | Q.S. |
| Methyl paraben U.S.P. | | 4.5 |
| Propyl paraben U.S.P. | | 1.0 |
| Polysorbate 80 U.S.P. | | 1.5 |
| Sorbital solition 70% U.S.P. | | 2500 |
| Buffer agent to adjust pH | Q.S. | Q.S |
| Water | Q.S. to 1 ml. | Q.S. to 5 ml. |

EXAMPLE 7

Tablets and Capsules Suitable for Oral Administration

Tablets and capsules containing the ingredients indicated below may be prepared by conventional techniques and are useful as cardiac stimulants at a dose of one or two tablets or capsules 1 to 4 times a day.

| Ingredient | Tablet | Capsule |
|---|---|---|
| (+)-3-(2,5-dihydroxyphenyl)-alanine | 50 | 100 |
| Tragacanth | 15 | |
| Lactose | 202.5 | 200 |
| Corn Starch | 20 | |
| Talcum | 10 | |
| Magnesium stearate | 2.5 | |
| TOTAL | 300.0 | 300.0 |

What is claimed is:

1. A method for the treatment of heart failure which comprises administering to an animal afflicted with heart failure an effective amount of 3-(2,5-dihydroxyphenyl)-alanine.

2. The method of claim 1 wherein a racemic mixture of 3-(2,5-dihydroxyphenyl)-alanine is the active ingredient.

3. The method of claim 1 wherein the (−) optical isomer of 3-(2,5-dihydroxyphenyl)-alanine is the active ingredient.

4. The method of claim 1 wherein the (+) optical isomer of 3-(2,5-dihydroxyphenyl)-alanine is the active ingredient.

* * * * *